(12) United States Patent
Peters

(10) Patent No.: US 7,075,299 B1
(45) Date of Patent: Jul. 11, 2006

(54) METHOD AND APPARATUS TO CORRECT AMPLITUDE MODULATION IN MULTI-ECHO MAGNETIC RESONANCE IMAGING

(75) Inventor: Robert D. Peters, Sussex, WI (US)

(73) Assignee: General Electric Company, Schenectady, NY (US)

( * ) Notice: Subject to any disclaimer, the term of this patent is extended or adjusted under 35 U.S.C. 154(b) by 25 days.

(21) Appl. No.: 10/707,433

(22) Filed: Dec. 12, 2003

(51) Int. Cl.
*G01V 3/00* (2006.01)
*A61B 5/055* (2006.01)

(52) U.S. Cl. ............... 324/309; 600/410; 600/411; 324/318

(58) Field of Classification Search ........ 324/300–322; 600/410; 341/139
See application file for complete search history.

(56) References Cited

U.S. PATENT DOCUMENTS

| | | | | |
|---|---|---|---|---|
| 4,684,891 A | * | 8/1987 | Feinberg | 324/309 |
| 4,746,860 A | * | 5/1988 | Satoh | 324/309 |
| 4,857,846 A | * | 8/1989 | Carlson | 324/309 |
| 4,859,946 A | * | 8/1989 | Kuhara | 324/309 |
| 4,939,463 A | * | 7/1990 | Sekihara et al. | 324/309 |
| 4,999,581 A | * | 3/1991 | Satoh | 324/309 |
| 5,315,249 A | * | 5/1994 | Le Roux et al. | 324/309 |
| 5,345,176 A | * | 9/1994 | LeRoux et al. | 324/309 |
| 5,451,876 A | * | 9/1995 | Sandford et al. | 324/322 |
| 5,517,122 A | * | 5/1996 | Chen | 324/322 |
| 5,578,923 A | * | 11/1996 | Chen | 324/309 |
| 5,621,321 A | * | 4/1997 | Liu et al. | 324/309 |
| 5,672,969 A | * | 9/1997 | Zhou et al. | 324/309 |
| 5,779,636 A | * | 7/1998 | Kanazawa | 600/410 |
| 5,923,168 A | * | 7/1999 | Zhou et al. | 324/309 |
| 6,043,654 A | * | 3/2000 | Liu et al. | 324/309 |
| 6,064,205 A | * | 5/2000 | Zhou et al. | 324/309 |
| 6,275,038 B1 | * | 8/2001 | Harvey | 324/309 |
| 6,275,458 B1 | * | 8/2001 | Wong et al. | 369/47.19 |
| 6,456,071 B1 | * | 9/2002 | Hennig | 324/307 |
| 6,528,998 B1 | * | 3/2003 | Zhou et al. | 324/309 |
| 6,541,970 B1 | * | 4/2003 | Takizawa et al. | 324/309 |
| 6,577,126 B1 | * | 6/2003 | Lehr | 324/307 |
| 6,586,935 B1 | * | 7/2003 | Ma et al. | 324/312 |
| 6,621,433 B1 | * | 9/2003 | Hertz | 341/139 |

(Continued)

FOREIGN PATENT DOCUMENTS

DE 4436801 A1 * 4/1995

(Continued)

OTHER PUBLICATIONS

Le Roux et al., article "Stabilization of Echo Amplitudes is FSE Sequences" Magnetic Resonance in Medicine vol. 30 1993 pp. 183-191.*

(Continued)

*Primary Examiner*—Diego Gutierrez
*Assistant Examiner*—Tiffany A. Fetzner
(74) *Attorney, Agent, or Firm*—Ziolkowski Patent Solutions Group, SC; Michael A. Della Penna; Carl B. Horton

(57) ABSTRACT

An imaging technique is disclosed for multi-echo, magnetic resonance imaging that addresses amplitude modulations, such as those caused by T2 decay and stimulated echo refocusing, in acquired MR data. Acquired MR data is corrected by non-phase encoded data such that amplitude modulations in the echo signal are addressed. Reducing the effects of amplitude modulations in the echo signal reduces ghosting and thereby improves image quality.

24 Claims, 8 Drawing Sheets

U.S. PATENT DOCUMENTS

| | | | |
|---|---|---|---|
| 6,657,933 B1 * | 12/2003 | Wong et al. | 369/47.35 |
| 6,700,375 B1 * | 3/2004 | Machida et al. | 324/314 |
| 6,850,063 B1 * | 2/2005 | Hennig | 324/314 |
| 6,853,190 B1 * | 2/2005 | Nittka et al. | 324/309 |
| 2002/0034138 A1 * | 3/2002 | Wong et al. | 369/47.35 |
| 2003/0109781 A1 * | 6/2003 | Zhang | 600/410 |
| 2004/0156284 A1 * | 8/2004 | Wong et al. | 369/47.35 |

FOREIGN PATENT DOCUMENTS

| | | |
|---|---|---|
| EP | 335534 A2 * | 10/1989 |
| EP | 335981 A1 * | 10/1989 |

OTHER PUBLICATIONS

Hennig, J. et al., RARE Imaging: A Fast Imaging Method for Clinical MR, Magnetic Resonance in Medicine, 1986, vol. 3, pp. 823-833.

Mulkern R. et al., Contrast Manipulation and Artifact Assessment of 2D and 3D RARE Sequences, Magnetic Resonance Imaging, 1990, vol. 8, pp. 557-566.

Riederer, S. et al., Fast Imaging Techniques, The Physics of MRI: 1992 AAPM Summer School Proceedings, American Institute of Physics, New York, pp. 206-233.

* cited by examiner

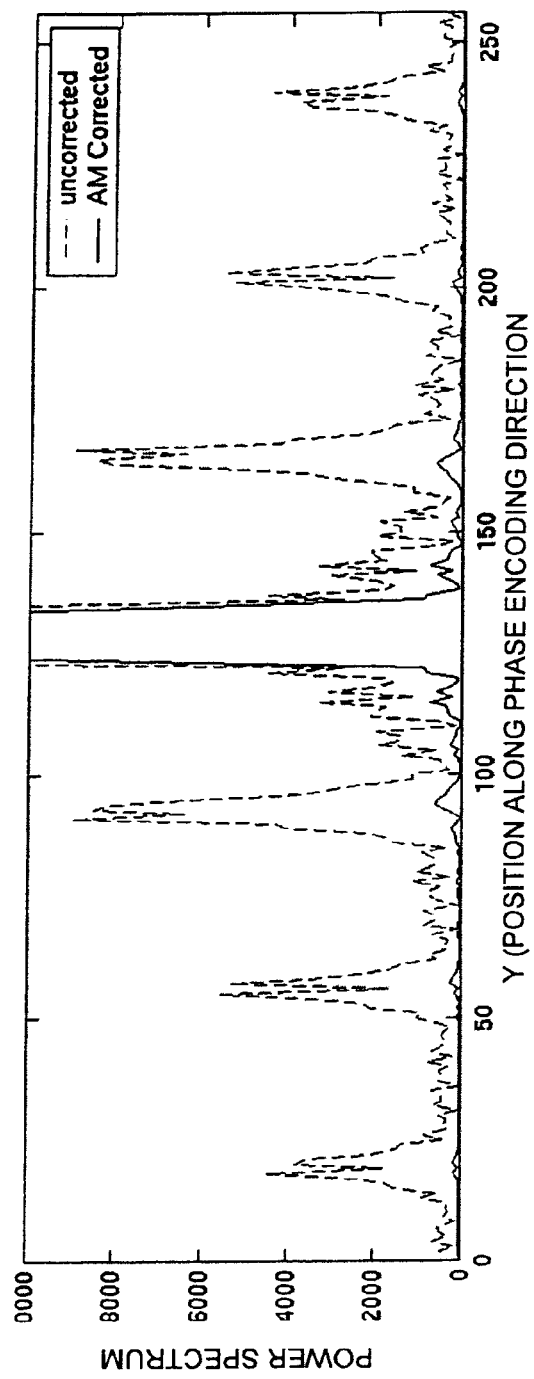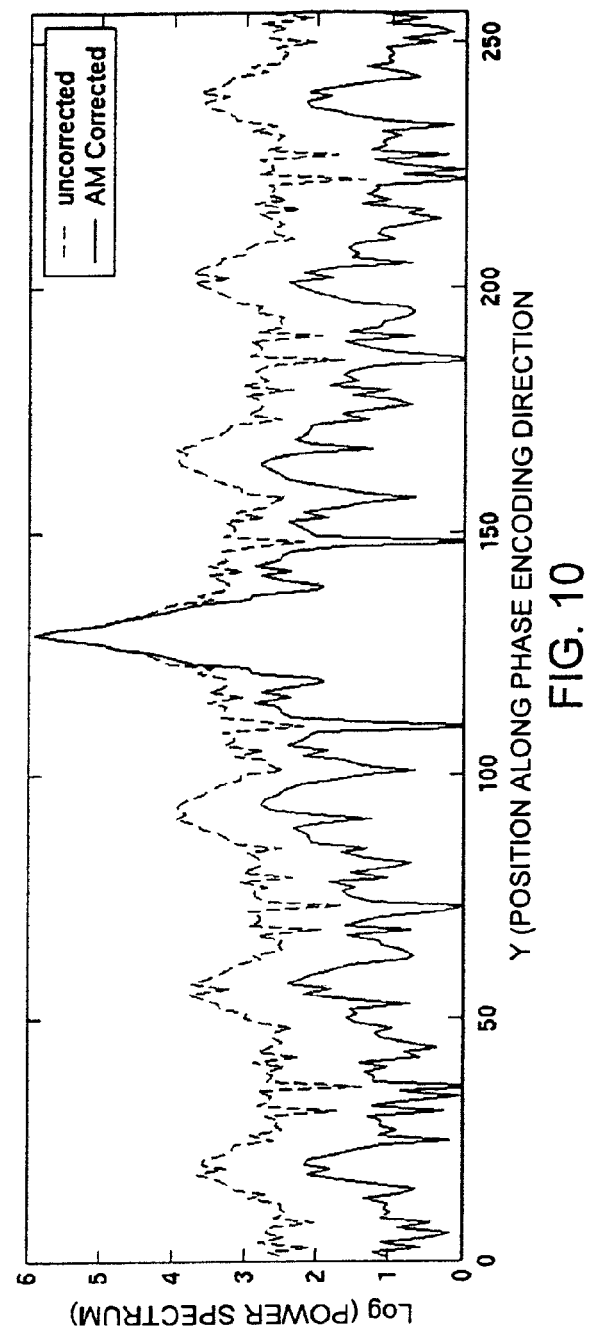

METHOD AND APPARATUS TO CORRECT AMPLITUDE MODULATION IN MULTI-ECHO MAGNETIC RESONANCE IMAGING

BACKGROUND OF INVENTION

The present invention relates generally to MR imaging and, more particularly, to a method and apparatus to correct amplitude modulation in multi-echo acquisition. The present invention is particularly applicable with fast spin echo (FSE) imaging.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

A number of imaging techniques have been developed to reduce scan time. Reduction in scan times has a number of advantages. For example, as scan time is reduced, patient throughput increases thereby allowing more subjects to be imaged in a given period of time. Additionally, it is generally well-known that some subjects, and in particular children, the elderly, and those that are claustrophobic, are prone to movement during the scanning technique. Despite repeated requests from the health care provider to the contrary, subjects often cannot resist the urge to move during the often lengthy scanning technique. This movement can introduce motion artifacts in the final reconstructed image thereby jeopardizing the diagnostic value of the final image. As such, scan time reduction has been shown to reduce subject motion induced artifacts.

One particular imaging technique that has been developed to reduce scan time is fast spin echo (FSE) imaging. FSE is a widely used technique because of its applicability for spin-spin weighted imaging, proton density imaging, and spin-lattice weighted imaging in relatively short periods of time. Moreover, FSE imaging may be implemented for neural imaging, body imaging, and extremity imaging.

FSE imaging utilizes a multi-echo, spin-echo pulse sequence where different parts of k-space are acquired by different spin echoes. For example, a four echo spin-echo sequence may be applied such that k-space is segmented into four sections. For example, the first echo may be used to fill a center of k-space, the second echo for k-space adjacent to the center, and so forth, with the data from the last spin-echo used to fill the outermost regions of k-space. Since four echoes rather than one are used to fill k-space, scan time, in this example, may be reduced four-fold.

Notwithstanding the advantages of FSE imaging, one particular drawback is ghosting that may occur in the final reconstructed image as a result amplitude modulation of the echo signal. Amplitude modulation may, for example, be caused by T2 decay along the multi-echo train. This ghosting is particularly problematic for high SNR imaging, such as with multi-channel array coils.

It would therefore be desirable to have a system and method capable of correcting for amplitude modulation in multi-echo acquisition.

BRIEF DESCRIPTION OF INVENTION

The present invention provides a system and method of correcting for amplitude modulation in multi-echo MR data acquisition that overcome the aforementioned drawbacks.

An imaging technique is disclosed that is particularly applicable with FSE imaging. Ghosting levels in FSE images are reduced by retrospectively addressing amplitude modulations, such as those caused by T2 decay and stimulated echo refocusing, in acquired MR data. The invention is particularly relevant for high SNR imaging protocols such as those that use multiple receiver coils. Further, by reducing ghosting and thereby improving image quality, fewer repeat scans would be required a significant contribution to increased throughput.

Therefore, in accordance with one aspect of the present invention, a method is introduced that includes the steps of acquiring MR data from multiple echoes in an echo train with a fast spin echo pulse sequence and correcting for amplitude modulation effects in the fast spin echo pulse sequence after data acquisition.

In accordance with another aspect of the invention, an MRI apparatus includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MRI apparatus also includes a computer programmed to acquire at least one set of reference MR data and determine a table of amplitude modulation correction values from the reference data.

In accordance with another aspect, the invention is embodied in a computer program stored on a computer readable storage medium and having instructions which, when executed by a computer, cause the computer to acquire non-phase encoded MR data and acquire phase encoded MR data from multiple echoes. The computer is also caused to modify the phase encoded MR data by the non-phase encoded MR data to correct amplitude modulation between the multiple echoes.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIGS. 9–10 are a series of graphs illustrating the effect of amplitude modulation correction on the data in accordance with the present invention.

DETAILED DESCRIPTION

Figure 1:
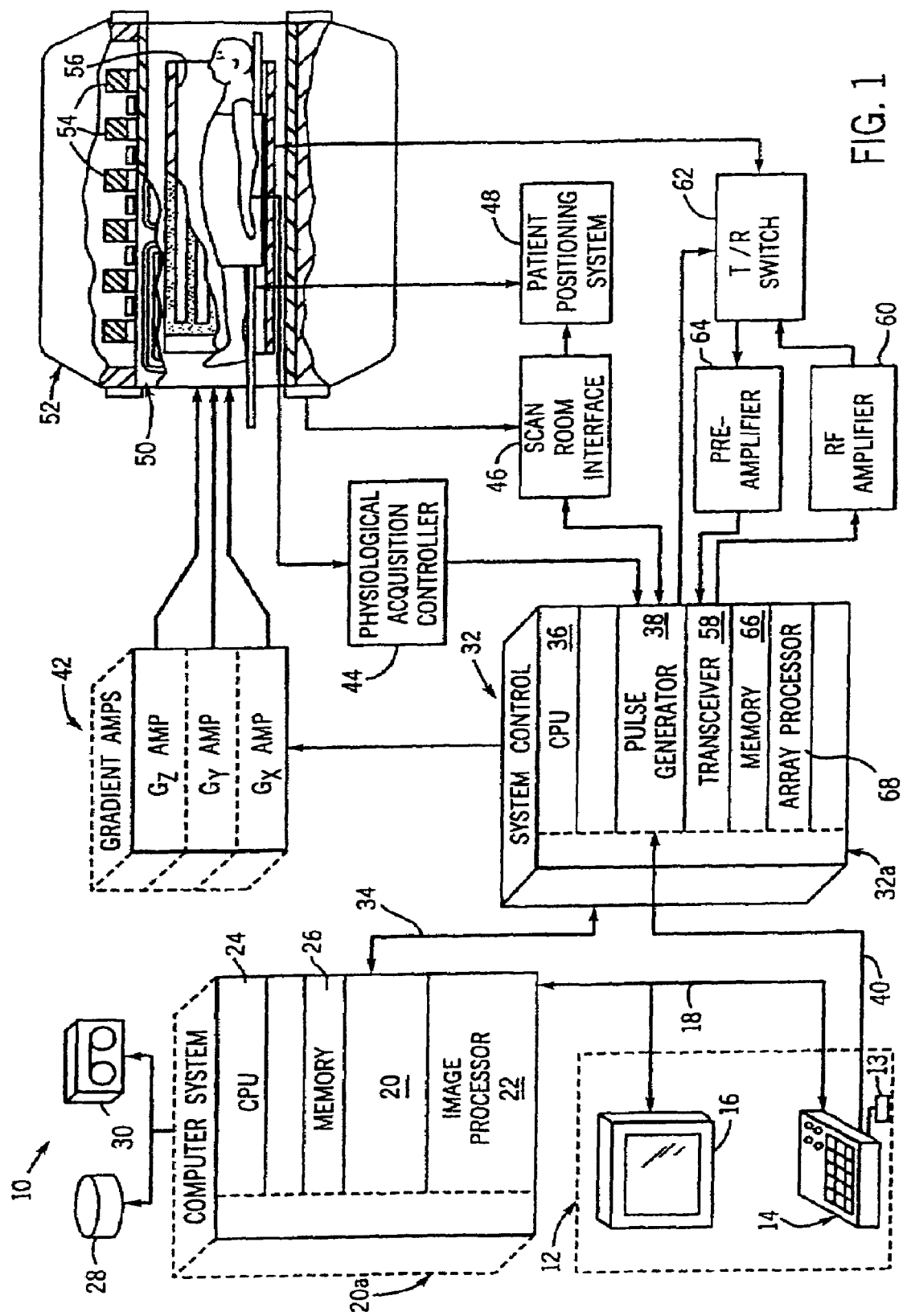
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil assembly 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil assembly 56 during the receive mode. The transmit/receive switch 62 can also enable a separate RF coil (for example, a surface coil) to be used in either the transmit or receive mode.

The MR signals picked up by the RF coil assembly 56, which may include multiple receiver elements, are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The system is capable of implementing an imaging technique to acquire MR data from a multi-echo train and correct for amplitude modulation in the echo train such as that caused by T2 decay or stimulated echo refocusing. For purposes of illustration only, the present invention will be described with respect to an FSE imaging technique.

Figure 2:
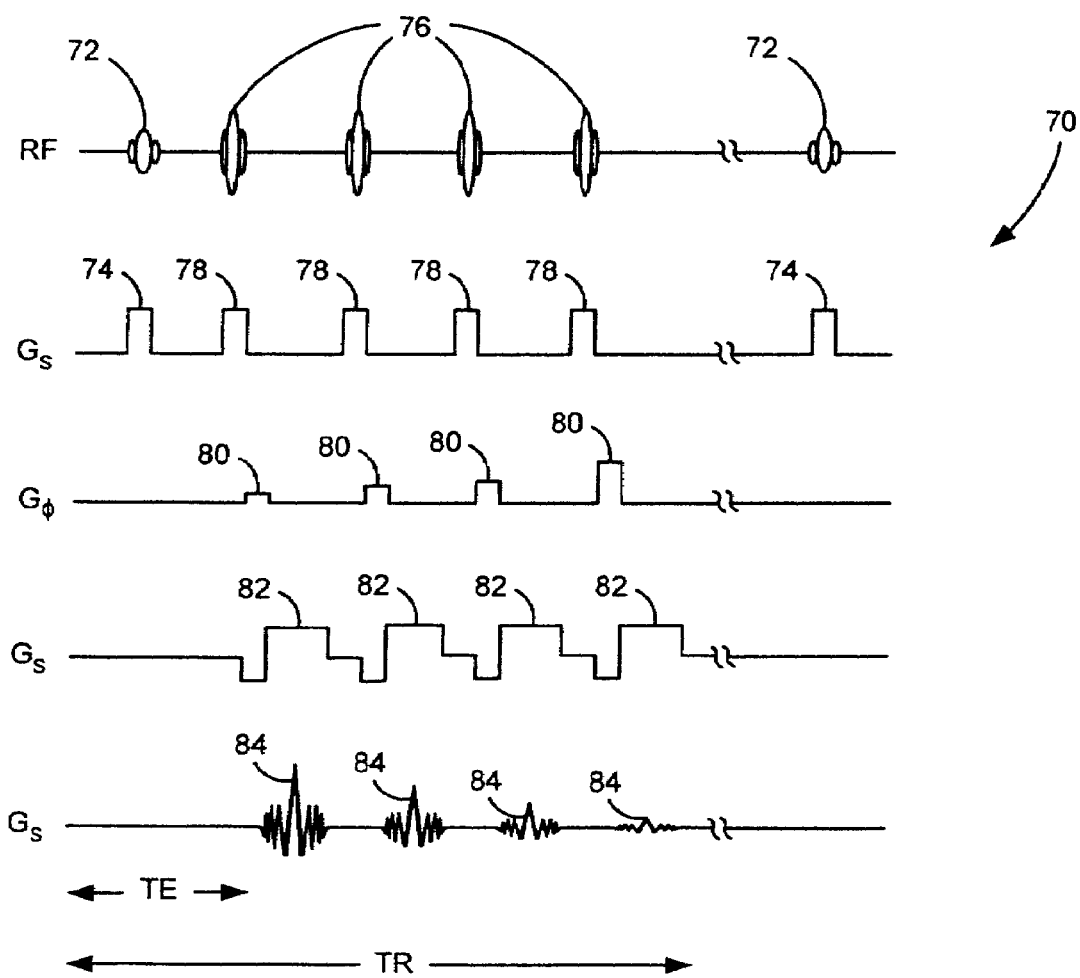
FIG. 2 is a graphic representation of a FSE pulse sequence.

An FSE sequence, such as that shown in FIG. 2, may be generally described as a multi-shot version of a spin echo experiment. With an FSE acquisition, each echo of an echo train length (ETL) is separately phase encoded. The echo signal amplitude in an FSE echo train generally decays according to well-known T2 relaxation effects, such that the echo signal at the $n^{th}$ echo is modulated by $\exp(-n\text{esp}/T2)$, with the echo spacing given by esp. In addition, echo signal amplitudes may show variations due to even-odd echo refocusing, which is a consequence of stimulated echo formation.

With FSE, a viewtable is used to relate the echo location with a specific phase encoding which determines the position of the echo within k-space. It should be noted that the present invention is independent of how the viewtable is generated. FSE imaging uses Fourier encoding in which discrete samples of the object's k-space, $S(k_x, k_y)$, are obtained through frequency encoding and phase encoding. This k-space represents the discrete Fourier transform of the MR signal density function, which is regarded as the object. Consequently, image reconstruction is achieved by performing an inverse Fourier transform to this sampled k-space.

With FSE, the k-space is amplitude modulated through techniques such as T2-decay or generation of stimulated echoes, and is denoted as $AM(k_y)$ and is a function of the phase-encoding parameter $k_y$. As such, the reconstructed FSE image can be modeled as:

$$\text{Image}(x,y) = F[AM(k_y) \cdot S(k_x,k_y)] \text{(Eqn. 1)}, = F[AM(k_y)] * F[S(k_x,k_y)]$$

where use has been made of the Fourier transform convolution theorem and F denotes the Fourier transform and * denotes convolution. It is evident that the amplitude modulation, $AM(k_y)$, can have an immediate effect on the reconstructed object and serves to modify the point spread function (PSF) along the $k_y$-direction (phase encoding direction) only. Note that in the above, the usual k-space, $S(k_x, k_y)$, includes PSF contributions along the $k_x$- and $k_y$-directions due to finite sampling (sinc term) and along the $k_x$-direction due to T2-decay (Lorentzian term).

If the $AM(k_y)$ function has significant high frequency components, then this can result in image ghosting where the spatial frequency of the ghosts is determined by $F\{AM\}(y)$. As an example, if a single echo were used (i.e. spin echo acquisition), then the $AM(k_y)$ function would be a constant with $F\{AM\}(y)$, a delta function, leaving no effect on the PSF of the reconstructed image and thus no additional ghosting.

Referring now to FIG. 2, an exemplary FSE pulse sequence 70 is shown. Sequence 70 reduces scan times (compared to conventional spin echo sequences) by phase encoding multiple echoes within an echo train of a single repetition time (TR). Typically, the ETL in FSE imaging ranges from two to 128 and represents a scan time reduction factor. For sequence 70, four echoes make up the ETL and, as such, relative to a standard spin echo sequence, sequence 70 yields a four-fold reduction in scan time.

As is well-known, sequence 70 is initiated by a slice selective 90 degree RF pulse 72 that is applied in conjunction with a slice selection gradient 74. A 180 degree refocusing pulse 76, in conjunction with a slice selection gradient pulse 78, is repeatedly applied throughout the TR. The number of refocusing pulses 76 coincides with the number of echoes 84 that will be sampled to fill k-space. Following application of each slice selection gradient pulse 78, a phase encoding gradient pulse 80 is applied. The phase encoding defines where in k-space MR data from a particular echo is placed. In this regard, the phase encoding gradient pulses 80 are incrementally changed in application during the TR interval. In the illustrated example, the strength of the phase encoding gradients 80 increases during the TR interval. One skilled in the art will readily appreciate that other phase encoding patterns may be employed and are considered within the scope of the invention, as is a 3D acquisition scheme that incorporates two phase encoding axes.

A frequency encoding gradient or "readout" pulse 82 is applied after each phase encoding pulse 80 so that an echo 84 may be sampled. It should be noted, however, that each echo experiences different amounts of T2 decay which can cause image contrast differences or "ghosting" compared with standard spin echo images acquired with similar TR and TE values. TE is defined as the time between the 90 degree pulse and the echo that receives zero phase encoding. Image artifacts may also result from the stimulated refocusing pulses. Notwithstanding these drawbacks, FSE imaging is often preferred because of the significant reductions in scan time that may be achieved. For example, a standard T2-weighted spin echo image (TR=2,000 msec, 256 phase encodes, one average) requires 8.5 minutes whereas a corresponding FSE with an ETL of four can be carried out in approximately 2.1 minutes.

Figure 3:
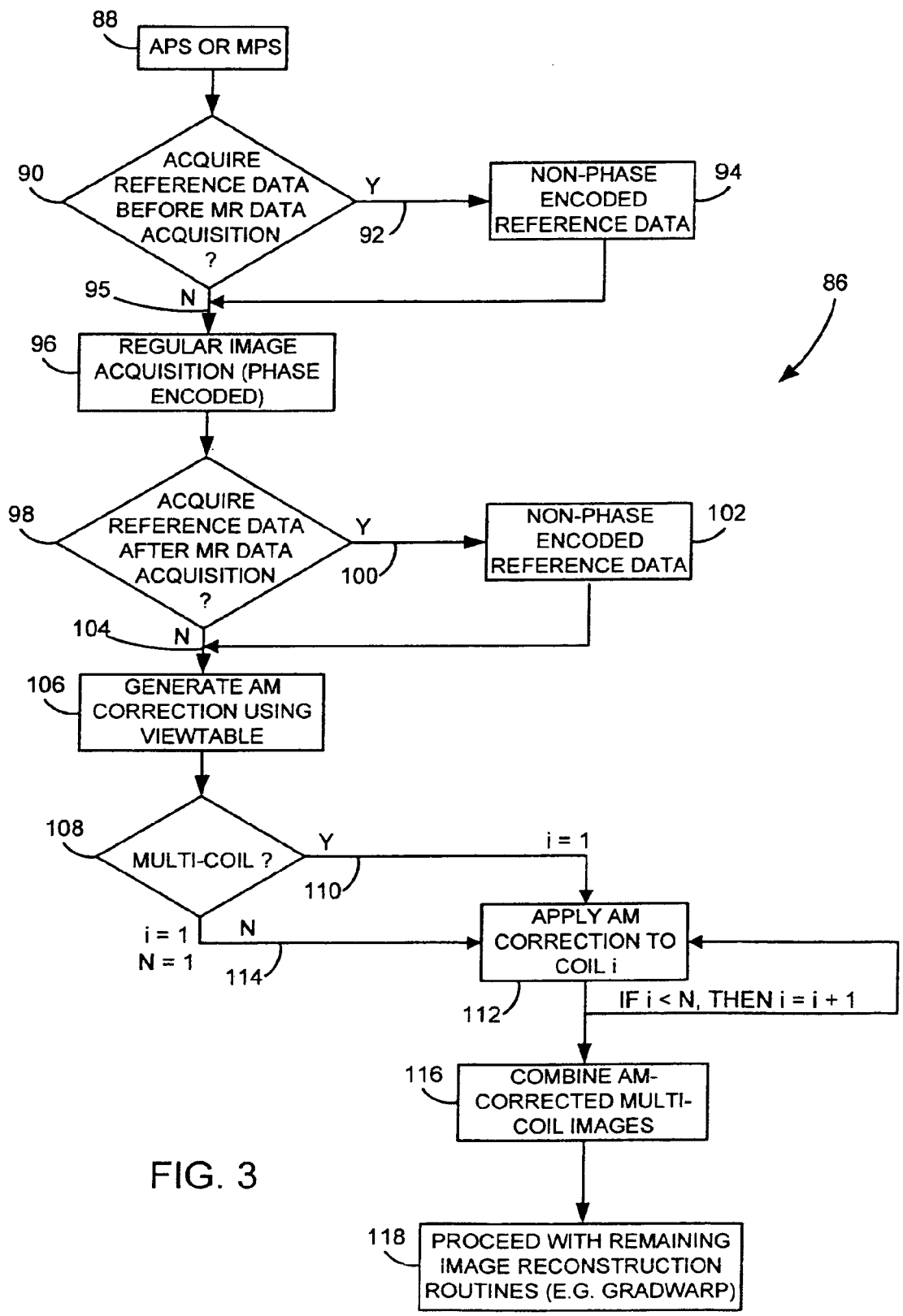
FIG. 3 is a flow chart setting forth the steps of an amplitude modulation correction technique in accordance with the present invention.

To address ghosting in FSE images resulting from amplitude modulation in the echo train, the present invention includes a retrospective technique that may be carried out as a set of instructions of a computer program. Further, the computer program may be bundled within a computer data signal that may be embodied in a carrier wave for uploading/downloading to an MR scanner system. Details of such a retrospective technique, and the actions of a computer programmed accordingly, are set forth in the technique shown in FIG. 3.

Technique 86 preferably begins with the execution of an auto or manual pre-scan calibrations 88. One skilled in the art will appreciate that an auto or manual pre-scan is not required for implementation of the present invention. Following a pre-scan at 88, a determination is made as to whether to acquire MR data before acquisition of reference MR data at 90. As will be described, the reference data (which includes non-phase encoded data) is used to correct for amplitude modulation in the echoes. If reference MR data is to be acquired before acquisition of MR data 90, 92, the technique continues to 94 with the acquisition of non-phase encoded data or reference MR data. The reference data includes non-phase encoded echoes or views that are used to estimate an amplitude modulation correction function. In this regard, the reference data represents the maximum achievable signal that a regular (phase-encoded) acquisition may attain.

To acquire the non-phase encoded reference MR data, phase encoding is turned off and receiver phase offsets (for off-center FOVs) are zeroed. At 94, reference data is acquired before the acquisition of MR data. As such, the reference views are acquired at the very beginning of the regular image sequence and, as mentioned, after execution of an auto or manual pre-scan. If discarded data acquisitions are played out, the last discarded acquisition may be used for the acquisition of the reference data. In this embodiment, scan time is not increased. However, it is contemplated for non-discarded acquisition protocols, that time could be added after the pre-scan for the acquisition of the reference MR data at a small scan time penalty.

Following the acquisition of the non-phase encoded data at 94, phase encoded MR data is acquired at 96 in accordance with standard FSE imaging techniques. As will be described, the reference MR data need not be acquired prior to MR data acquisition. The reference data may be acquired after MR data acquisition. As such, if reference data is not to be acquired before MR data acquisition 90, 95, technique 86 continues at 96 with the acquisition of phase encoded MR data.

Thereafter, technique 86 continues at 98 whereupon a decision is made whether to acquire non-phase encoded data after acquisition of the MR data at 96. If reference data is also to be acquired after MR data acquisition 98, 100, technique 86 continues at 102 where additional non-phase encoded reference data is acquired. However, it is contemplated that only the reference data acquired at 94 be used to correct amplitude modulation and, as such, it is not necessary to acquire reference data following acquisition of the phase encoded MR data 98, 104. It is preferred however that reference data be acquired before and after MR data acquisition. Acquisition of reference data prior to and after MR data acquisition may serve to average out any non-steady state behavior in the echo train or any potential temporal drift in the stability of the MR system. It is noted however that scan time is minimally increased for the acquisition of reference data following acquisition of the phase encoded MR data. The amount of increase is the product of the repetition time (TR) of the pulse sequence and the number of times the sequence is repeated.

Once reference data and phase encoded MR data have been acquired, an amplitude modulation (AM) correction table is generated at 106. As mentioned, the reference data includes non-phase encoded echoes or views that are used to estimate an amplitude modulation function, $AM(k_y)$. These signals represent the maximum achievable signal that the phase encoding acquisition may attain. The reference data is analyzed to determine echo signal amplitudes. The amplitude values along the echo train together with viewtables are used to generate an estimate of $AM(k_y)$. If more than one reference dataset is acquired, i.e. reference data before and after MR data acquisition, then a single estimate of $AM(k_y)$ is generated by averaging the two data sets. From this estimate, a smoothing or filtering operation can be applied to remove discontinuities, as demonstrated in FIG. 6.

To reduce the impact of the $AM(k_y)$ function on the PSF, an AM correction table is generated. The correction table may be generated according to a number of techniques. One such technique involves taking the ratio of the two curves shown in FIG. 6 and attenuating the region at the edges of k-space, which represent high spatial frequencies and typically contains little signal.

The present invention is applicable with MR systems having multiple receiver coils. In this regard, the technique continues at 108 to determine if MR data was acquired with multiple coils. If so 108, 110, the AM correction is generated and applied to each coil independently. Application of the AM correction table to phase encoded k-space includes multiplying each k-space view with an appropriate entry in the AM correction table, which depends on the $k_y$ position of the phase encoded data in k-space.

AM correction is applied to coil i at 112. Once AM correction is applied to the MR data acquired from coil i, an AM correction table is generated and applied to coil i+1. Accordingly, different coil magnitude sensitivities are taken into account in the amplitude correction technique. If MR data is acquired with a single receiver coil 108, 114, the AM correction table is applied to the entire phase encoded MR data or k-space for the single coil. It should be noted that the AM correction table is applied to each k-space prior to Fourier transformation of the k-space.

For multiple receiver coil data acquisition, the amplitude modulation corrected views are then combined at 116 by taking the square root of the sum of the squares of the individual coil-derived images. Other combination techniques may be used and are contemplated. The combined image, which has been corrected for amplitude modulation in the echo train, may then be processed at 118 in accordance with well-known and customary reconstruction routines, e.g. GRADWARP. GRADWARP is a trademark of General Electric Company, Waukesha, Wis.

GRADWARP is a reconstruction technique used to correct geometric distortions in acquired MR data. Specifically, GRADWARP is a procedure whereby gradient non-uniformity is corrected. When gradients of a magnetic field vary, i.e. non-uniform, the resulting images may be distorted, or warped. This problem is typically accentuated with increasing distance from the isocenter of the magnet. The resulting images, however, may be corrected using GRADWARP or similar correction technique.

It is preferred that generation of the AM correction table and its application with either a single coil or multi-coil MR system be carried out with an array processor in a post-processing manner that is transparent to the user. As such, in one preferred embodiment, the user is only required to enter customary scanning parameters (TR, TE, ETL, and the like) and temporally defines the acquisition of the reference data.

Experimental results consistent with the AM correction technique set forth above will now be described with respect to the imaging of a spherical phantom filled with a $NiCl_2$ doped solution. A GE Medical Systems 1.5T scanner and an 8-channel head coil were used for data acquisition. MR data was acquired with the following parameters: 1 slice, 256 phase encodes, 2 NEX, TE/TR/Bw=50/1000/15.6, ETL=20, esp=13.28 ms, lope_echo=4. One skilled in the art will readily appreciate that the above parameters are for illustrative purposes and that the present invention is applicable with pulse sequences defined by other scan parameters.

Figure 4:
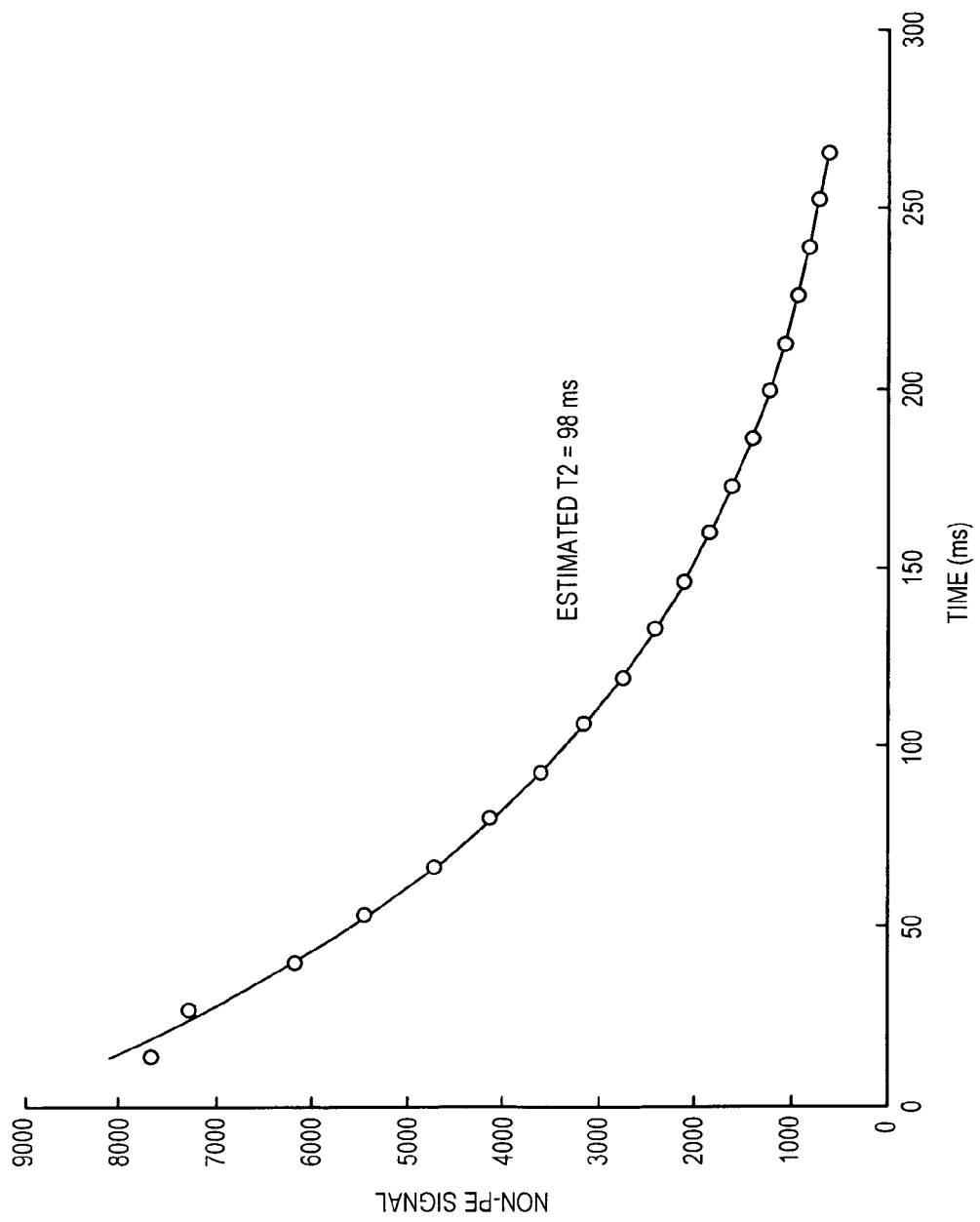
FIG. 4 is a graph illustrating decreasing amplitude of an echo signal due to T2 decay.

Referring to FIG. 4, a signal decay curve of a FSE echo train in a sphere phantom is shown. The data demonstrates the decreasing amplitude of a non-phase encoded echo signal due to T2 decay over time. The solid line represents an estimated T2 decay curve in which T2 was estimated at 98 ms and, as shown, is consistent with $NiCl_2$ doped solution in the phantom. It should be noted, however, that the present invention does not require estimation of T2.

Figure 5:
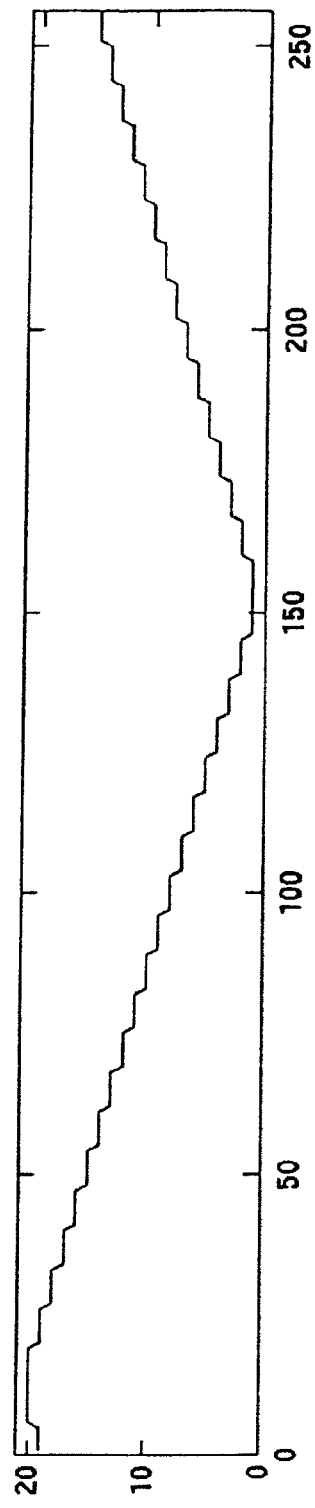
FIGS. 5–8 are a series of graphs illustrating an amplitude correction technique in accordance with the present invention.
Figure 6:
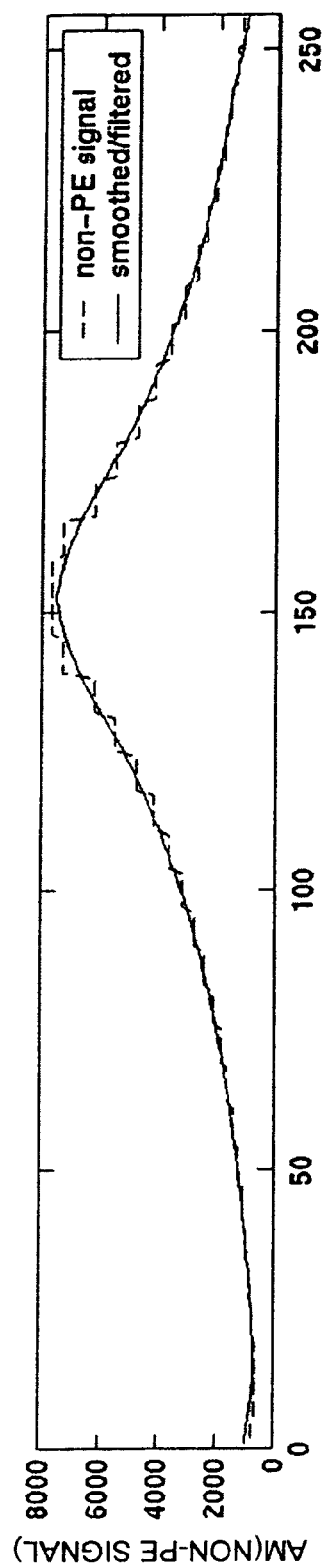
Figure 7:
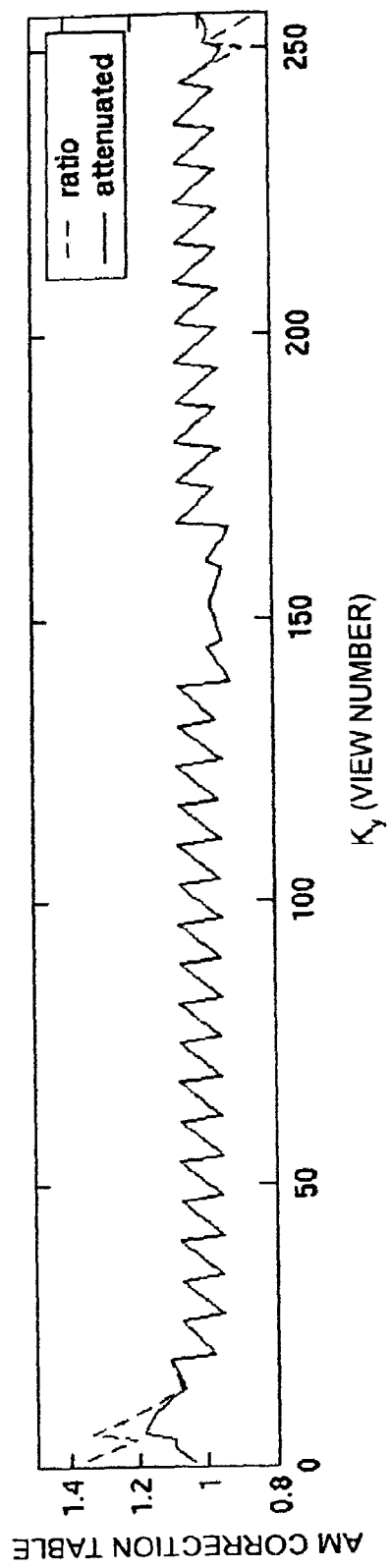
Figure 8:
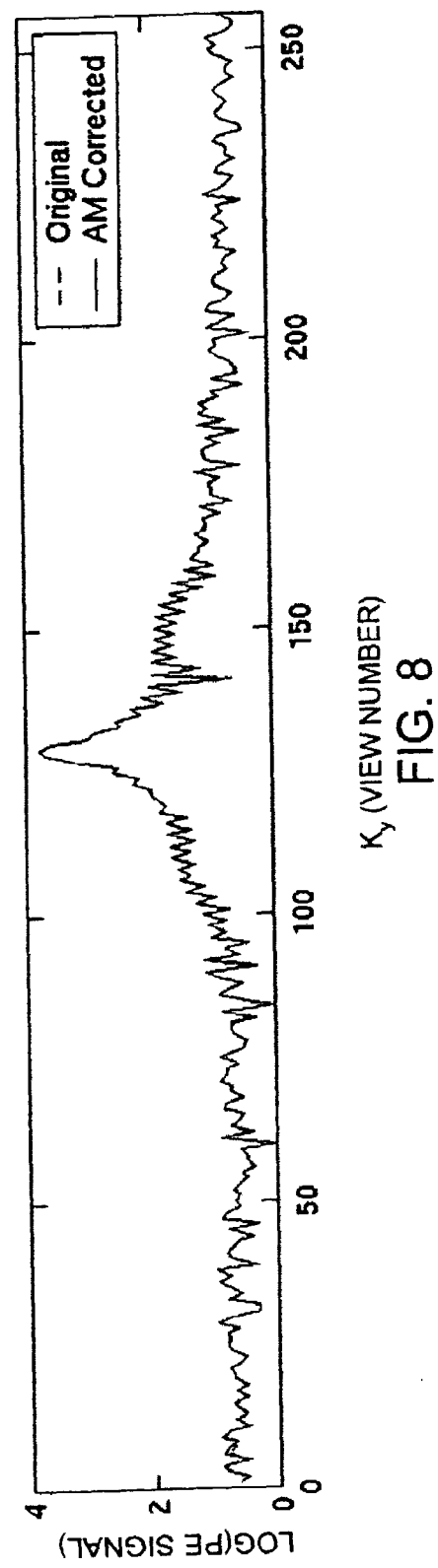

Referring now to FIGS. 5–8, a series of curves illustrate application of the present invention in the above-defined example. FIG. 5 corresponds to a viewtable which associates each echo within the echo train with a location in k-space or view (along the phase encoding direction). In this case, with the chosen TE and echo spacing of the FSE sequence, the low-order phase encode (lope_echo) was four. FIG. 6 includes a pair of curves which illustrates that for a single echo train of non-phase encoded data, an estimate of the $AM(k_y)$ function can be made (solid line) which follows the step-wise behavior in the echo train due to T2 decay. From this estimate of $AM(k_y)$, a smoothing operating was applied to remove discontinuities. FIG. 7 represents, from a ratio of the two curves in FIG. 6, the AM correction table to be applied to the regular (phase encoded) image data. As illustrated in FIG. 8, application of the AM correction table produces no distinguishable spatial differences between the original and AM corrected k-space which suggests that no specific spatial frequencies are attenuated or suppressed by application of the AM correction values to the acquired MR data.

FIGS. 9–10 illustrate the Fourier transform of the estimated and corrected amplitude modulation function. FIG. 9 corresponds to a linear representation of the power spectra of the two curves illustrated in FIG. 6. FIG. 10 corresponds to a logarithmic representation of the power spectra of the two curves illustrated in FIG. 6. More specifically, FIGS. 9 and 10 illustrate the PSF contribution (along the phase encoding direction) attributable to the FSE amplitude modulation. In this example, an attenuation factor of 10 of side lobes was realized with the AM correction technique described herein.

Figure 12:
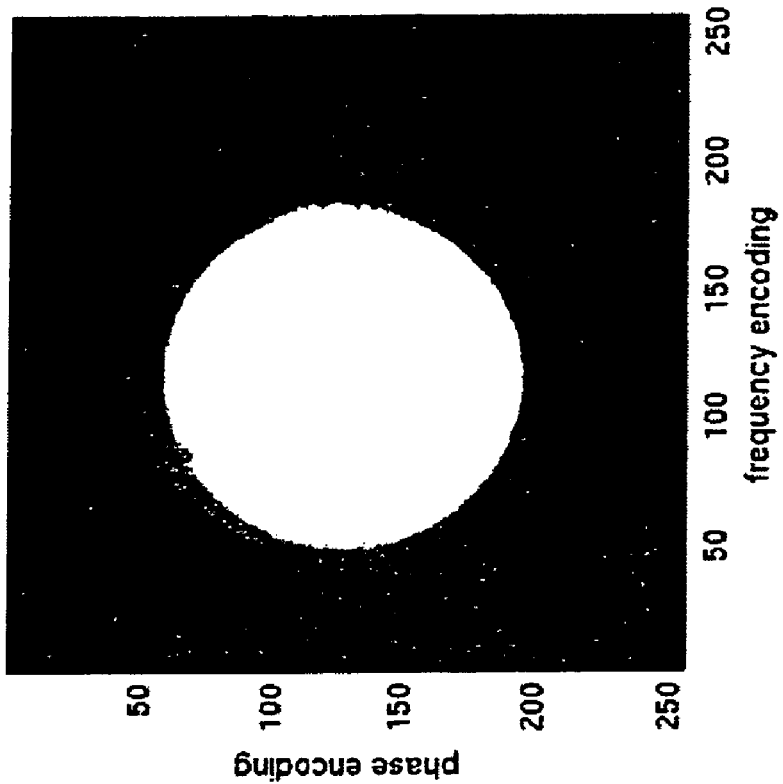
FIGS. 11–12 are a pair of reconstructed images of a sphere phantom illustrating ghosting differences between uncorrected and corrected MR data.
Figure 11:
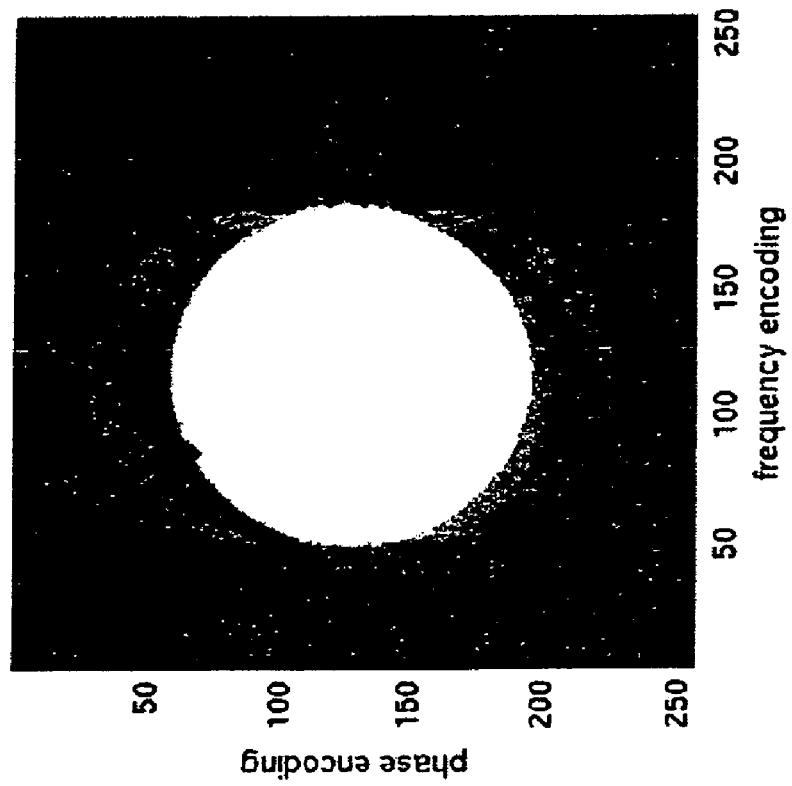

Referring now to FIGS. 11–12, a pair of images illustrates ghosting in an image generated from AM corrected FSE data (FIG. 12) relative to an image generated from non-corrected FSE data (FIG. 11). Clearly, ghosting is considerably more prevalent in the image of FIG. 11 when compared to the image of FIG. 12 the AM corrected image. It should be noted that both images were windowed/leveled equally to illustrate ghosting outside the phantom.

The present invention is directed to a method of reducing the impact of the amplitude modulation on overall PSF in FSE imaging. This approach reduces ghosting artifacts, is independent of the viewtable that is used, and causes no significant loss of spatial resolution information in the image.

Therefore, the present invention includes a method of MR imaging that includes acquiring MR data from multiple echoes in an echo train with a fast spin echo pulse sequence and correcting for amplitude modulation effects in the fast spin echo pulse sequence after data acquisition.

An MRI apparatus is also disclosed and includes an MRI system having a plurality of gradient coils positioned about a bore of a magnet to impress a polarizing magnetic field. An RF transceiver system and an RF switch are controlled by a pulse module to transmit and receive RF signals to and from an RF coil assembly to acquire MR images. The MRI apparatus also includes a computer programmed to acquire at least one set of reference MR data and determine a table of amplitude modulation correction values from the reference data. The computer is also programmed to modify acquired k-space MR data by the table of amplitude modulation correction values.

In accordance with another embodiment, the invention is embodied in a computer program stored on a computer readable storage medium and having instructions which, when executed by a computer, cause the computer to acquire non-phase encoded MR data and acquire phase encoded MR data from multiple echoes. The computer is also caused to modify the phase encoded MR data by the non-phase encoded MR data to correct amplitude modulation between the multiple echoes.

The present invention has been described in terms of the preferred embodiment, and it is recognized that equivalents, alternatives, and modifications, aside from those expressly stated, are possible and within the scope of the appending claims.

What is claimed is:

1. A method comprising the steps of:
   acquiring k-space data from multiple echoes in an echo train with a fast spin echo pulse sequence; then
   correcting the acquired k-space data for amplitude modulation effects in the fast spin echo pulse sequence; and
   2D Fourier transforming the corrected k-space data to form an image space from which an image is reconstructed.

2. The method of claim 1 wherein the step of correcting includes the steps of:
   acquiring at least one set of reference k-space data;
   determining a table of amplitude modulation correction values; and
   applying at least a portion of the table to the acquired k-space data.

3. The method of claim 2 further comprising the steps of acquiring at least one set of reference k-space data before and after acquisition of the k-space data.

4. The method of claim 2 further comprising the steps of:
   acquiring at least one set of reference k-space data before acquisition of the k-space data; and
   acquiring a second portion of the at least one set of reference k-space data after acquisition of the k-space data.

5. The method of claim 2 wherein the at least one set of reference k-space data includes non-phase encoded data.

6. The method of claim 2 wherein the steps of applying includes the steps of:
   multiplying each k-space view of the acquired k-space data by a correction value in a corresponding ky location in the table; and
   carrying out the steps of multiplying prior to transformation of the acquired k-space data from k-space to image space.

7. The method of claim 2 wherein the at least one set of reference data includes two sets of reference data, and further comprising the steps of averaging the two sets of reference data to determine the table of correction values.

8. The method of claim 5 wherein the at least one set of reference data represents a maximum achievable signal that the acquired phase encoded k-space data can attain.

9. The method of claim 1 wherein the k-space data is acquired via multiple receiver coils, and further comprising the steps of correcting for amplitude modulation effects in the k-space data from each receiver coil independently.

10. The method of claim 9 further comprising the steps of generating a combined image from corrected image data from each receiver coil.

11. An MRI apparatus comprising:
   a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and
   a computer programmed to:
      (A) acquire at least one set of reference MR data;
      (B) determine a table of amplitude modulation correction values from the reference MR data;
      (C) acquire MR data with a fast spin echo pulse sequence; and then
      (D) modify the acquired MR data while the MR data is entirely in k-space by the table of amplitude modulation correction values to account for amplitude modulation effects in a fast spin echo pulse sequence played out to acquire the MR data.

12. The MRI apparatus of claim 11 wherein the computer is further programmed to acquire the at least one set of reference MR data from one or more discarded acquisitions played out prior to or after acquisition of the MR data.

13. The MRI apparatus of claim 11 wherein the computer is further programmed to acquire portions of the at least one set of reference MR data prior to and after acquisition of the MR data.

14. The MRI apparatus of claim 11 wherein the at least one set of reference MR data includes non-phase encoded data and the acquired MR data is modified while in k-space.

15. The MRI apparatus of claim 11 wherein the RF coil assembly includes a phased array of receiver coils.

16. The MRI apparatus of claim 15 wherein the computer is further programmed to carry out acts (A)–(D) independently for each receiver coil.

17. The MRI apparatus of claim 11 wherein the computer is further programmed to generate an image space from the modified MR data.

18. A computer readable storage medium having a computer program to execute a fast spin echo pulse sequence stored thereon and representing a set of instructions that when executed by a computer causes the computer to:
   acquire non-phase encoded MR data;
   acquire phase encoded MR data from multiple echoes with the fast spin echo pulse sequence;
   generate a set of amplitude correction values from the non-phase encoded MR data;
   arrange the set of amplitude correction values in a table dimensionally equivalent to a k-space of phase encoded MR data; and then
   modify the phase encoded MR data by the non-phase encoded MR data to correct amplitude modulation between the multiple echoes by modifying each data point of k-space with a similarly positioned amplitude correction value.

19. The computer readable storage medium of claim 18 wherein the set of instructions further causes the computer to acquire the non-phase encoded MR data from a series of discarded acquisitions played out before or after acquisition of the phase encoded MR data.

20. The computer readable storage medium of claim 18 wherein the phase encoded data includes one of 2D and 3D MR data.

21. The computer readable storage medium of claim 18 wherein the non-phase encoded MR data represents a maximum achievable signal that the phase encoded MR data can attain.

22. The computer readable storage medium of claim 18 wherein the set of instructions further causes the computer to amplitude correct acquired phased encoded MR data without increasing scan time.

23. The computer readable storage medium of claim 18 wherein the set of instructions further causes the computer to carry out a pre-scan of a subject and acquire the non-phase encoded MR data after the pre-scan but before acquisition of the phase encoded MR data.

24. The computer readable storage medium of claim 18 incorporated into a computer data signal embodied in a carrier wave that is uploadable/downloadable to an MR imaging system.

* * * * *